United States Patent
Pan

(10) Patent No.: US 7,362,421 B2
(45) Date of Patent: Apr. 22, 2008

(54) ANALYSIS OF SIGNAL OSCILLATION PATTERNS

(75) Inventor: Gang Pan, Maple Grove, MN (US)

(73) Assignee: TSI Incorporated, St. Paul, MN (US)

( * ) Notice: Subject to any disclaimer, the term of this patent is extended or adjusted under 35 U.S.C. 154(b) by 0 days.

(21) Appl. No.: 11/515,104

(22) Filed: Sep. 1, 2006

(65) Prior Publication Data

US 2007/0047836 A1 Mar. 1, 2007

Related U.S. Application Data

(60) Provisional application No. 60/713,790, filed on Sep. 1, 2005.

(51) Int. Cl.
*G01P 3/36* (2006.01)
(52) U.S. Cl. .................................. 356/28.5
(58) Field of Classification Search ............... 356/28.5
See application file for complete search history.

(56) References Cited

U.S. PATENT DOCUMENTS 6,587,208 B2 * 7/2003 Maeda et al. .............. 356/496
2002/0180954 A1 * 12/2002 Qian et al. ................. 356/73.1

OTHER PUBLICATIONS

Merklinger, The Scheimpflug Principle—Part 1, *Shutterbug*, Nov. 1992, pp. 3.
Nitehawk, *SM 5 BSZ—Sliding FFT and DSP Filtering*, www.nitehawk.com/sm5fsz/slfft/slfft.htm, Apr. 25, 1997, pp. 9.
Pan et al., Simultaneous Global Size and Velocity Measurement of Droplets and Sprays, 20th Annual Conference on Liquid Atomization and Spray Systems, *ILASS*, Aug. 2005, pp. 6.

* cited by examiner

*Primary Examiner*—Thomas H. Tarcza
*Assistant Examiner*—Luke D. Ratcliffe
(74) *Attorney, Agent, or Firm*—Patterson, Thuente, Skaar & Christensen, P.A.

(57) ABSTRACT

A method for identifying and determining the frequency of scattered radiation fringe patterns for applications such as particle or droplet sizing and laser Doppler velocimetry. The method utilizes a series of windowed Fourier transforms performed on an intensity profile of the scattered radiation to locate a segment where a fringe pattern is located on the intensity profile. A standard Fourier transform is then performed on the segment to determine a dominant frequency of the fringe pattern, from which a physical quantity such as diameter or velocity of the particle or droplet may be derived. The method may be utilized with a line or an array sensor to measure the fringe patterns in a spatial domain, or with a point detector to measure the fringe patterns in the time domain.

16 Claims, 7 Drawing Sheets

ANALYSIS OF SIGNAL OSCILLATION PATTERNS

RELATED APPLICATION

This application claims benefit of U.S. Provisional Application Ser. No. 60/713,790, filed Sep. 1, 2005, which is hereby fully incorporated herein by reference.

FIELD OF THE INVENTION

The present invention relates to systems and processes for analyzing fringe patterns or oscillation patterns derived from scattered coherent energy, and more particularly to an apparatus and method for analyzing the fringe patterns presented by moderate to high density target population fields. The apparatus and method hereof are particularly well suited for measuring the physical characteristics of airborne particles and droplets based on the frequency or spacing of interference fringes.

BACKGROUND OF THE INVENTION

A variety of particle and droplet characterizing techniques involve the analysis of fringe patterns or oscillation patterns scattered by an irradiated particle or droplet. For example, interferometric particle sizing is based on the interference of laser energy reflected and refracted from transparent spherical particles. The angular spacing of the interference fringes is inversely proportional to the droplet diameter.

Some interferometric particle sizing systems utilize a sheet-shaped laser beam that is applied to a measurement space, and out-of-focus images of droplets irradiated with the laser beam are captured. A known method for fringe pattern analysis in the out-of-focus images involves the so-called "edge detection" technique. The out-of-focus image corresponding to each droplet is distinguished and extracted from the original image by detecting the edge of the fringe pattern. Since the relationship between the angular spacing of the fringe pattern and the diameter of the droplet is known, the diameter of the droplet is determined by counting the number of interference fringes in the extracted fringe pattern.

U.S. Pat. No. 6,587,208 to Maeda, et al. (Maeda) discloses an improvement on the edge detection technique. The Maeda method calls for the use of a cylindrical lens to compress an otherwise disk-shaped fringe pattern into a line oscillation pattern without significantly altering the spacing of the fringes. The line oscillation pattern enables the use of a low-pass filter to convert the oscillation pattern to a one-dimensional Gaussian pattern, from which individual fringe patterns can be distinguished and extracted. Maeda also discloses the use of a fast Fourier transform to establish the number of fringes in an extracted fringe pattern.

Another technique that may involve fringe pattern analysis is laser Doppler velocimetry (LDV). Particles pass through a viewing volume determined by the intersection of two laser beams. Light scattered by the particles passing through the viewing volume is detected, and the particle velocity, which is inversely proportional to the frequency of the scattered fringe pattern, is determined.

A problem arises with the aforementioned sizing and velocity techniques when the population density of a particle or droplet field is high enough to cause frequent overlapping of corresponding fringe patterns. Existing techniques cannot discern between overlapping fringe patterns, and instead presumes the overlapping fringe patterns to be a single fringe pattern. An error results in the fringe count (and therefore the size determination) as well as in the frequency and position determination of the corresponding particles.

SUMMARY OF THE INVENTION

To address these and other concerns, the present invention provides a system and process for analyzing fringe pattern data, i.e. the oscillations in the intensity of interfering scattered monochromatic energy, such as the light or other electromagnetic radiation reflected and refracted by droplets. Hereinafter, "intensity" is defined as a radiative energy passing through an area per unit solid angle, per unit of the area projected normal to the direction of passage, and per unit time, or any parameter proportional thereto, such as radiative flux. The fringe pattern data preferably are presented as variations in intensity, over space (as in the case of interferometric particle sizing), or over time (as in the case of laser Doppler velocimetry).

Initially, a windowed Fourier transform is applied to the fringe pattern data. If time or distance is presented as the horizontal axis or the abscissa parameter of a plot or profile in which the vertical axis or ordinate represents intensity, a "window" of the fringe pattern data can be pictured as a vertically extending subset or "slice" having a horizontal width along the abscissa (e.g. in pixels or samples representing micrometers or milliseconds) less than the pixel size or width of the fringe pattern data as a whole, and more particularly similar in width to the anticipated fringe pattern width. Each window is characterized by a midpoint along the abscissa, and successive windows are based on progressive shifts of the center point along the abscissa of the data field. Adjacent windows preferably overlap one another. An exemplary window width is in the range of 64 to 128 pixels or samples, and the shift from one window position to the next is 1 to 4 pixels or samples.

With respect to each window, a Fourier transform is performed after multiplying the fringe pattern data by a window function. The window function is non-zero within the window width, and zero outside the window.

The result is a set of power-frequency spectra, one associated with each window position (hereinafter referred to as a window power-frequency spectrum). For convenience, "frequency" is hereby defined as a spatial frequency having units of inverse length, a periodic frequency having units of inverse time, or a dimensionless angular spacing. The power-frequency spectra are aggregated to give a composite distribution of the power in the frequency-space (or frequency-time) domain. In connection with performing a Fourier transform on each window, criteria can be used to reject points unlikely to be part of a fringe, e.g. due to intensity less than a threshold, or the absence of any substantial intensity oscillation.

Next, each window power-frequency spectrum is used to locate a dominant or "peak" frequency (i.e. the frequency where the electromagnetic radiation is at highest power) associated with each window.

Based on the sensed peak frequencies, fringe patterns are located by generating a plot or profile of the peak frequencies in a frequency-space or frequency-time domain. Rejected points are assigned a frequency of zero. Because the frequency of fringe patterns is substantially uniform, each fringe pattern appears on the plot or profile as a horizontal (zero slope) line, corresponding in length to the location or duration of the associated fringe pattern. This accurately positions the fringes along the space (or time) axis, and facilitates distinguishing segments of the original fringe pattern data, one segment associated with each fringe pattern, to be extracted from the original data.

Each fringe pattern data segment is individually analyzed to determine the fringe pattern frequency. Preferably this is done in a frequency domain by performing a standard Fourier transform on the fringe pattern data segment. Thus, the frequency of each fringe pattern is determined by using the power spectrum produced from the associated fringe pattern data segment, providing an accurate determination of fringe pattern frequency or angular spacing, for conversion to particle size or particle velocity or other physical information of interest, depending on the application.

As an alternative to the standard Fourier transform, each fringe pattern data segment can be analyzed in a space or time domain by autocorrelation.

DETAILED DESCRIPTION OF THE INVENTION

Figure 1:
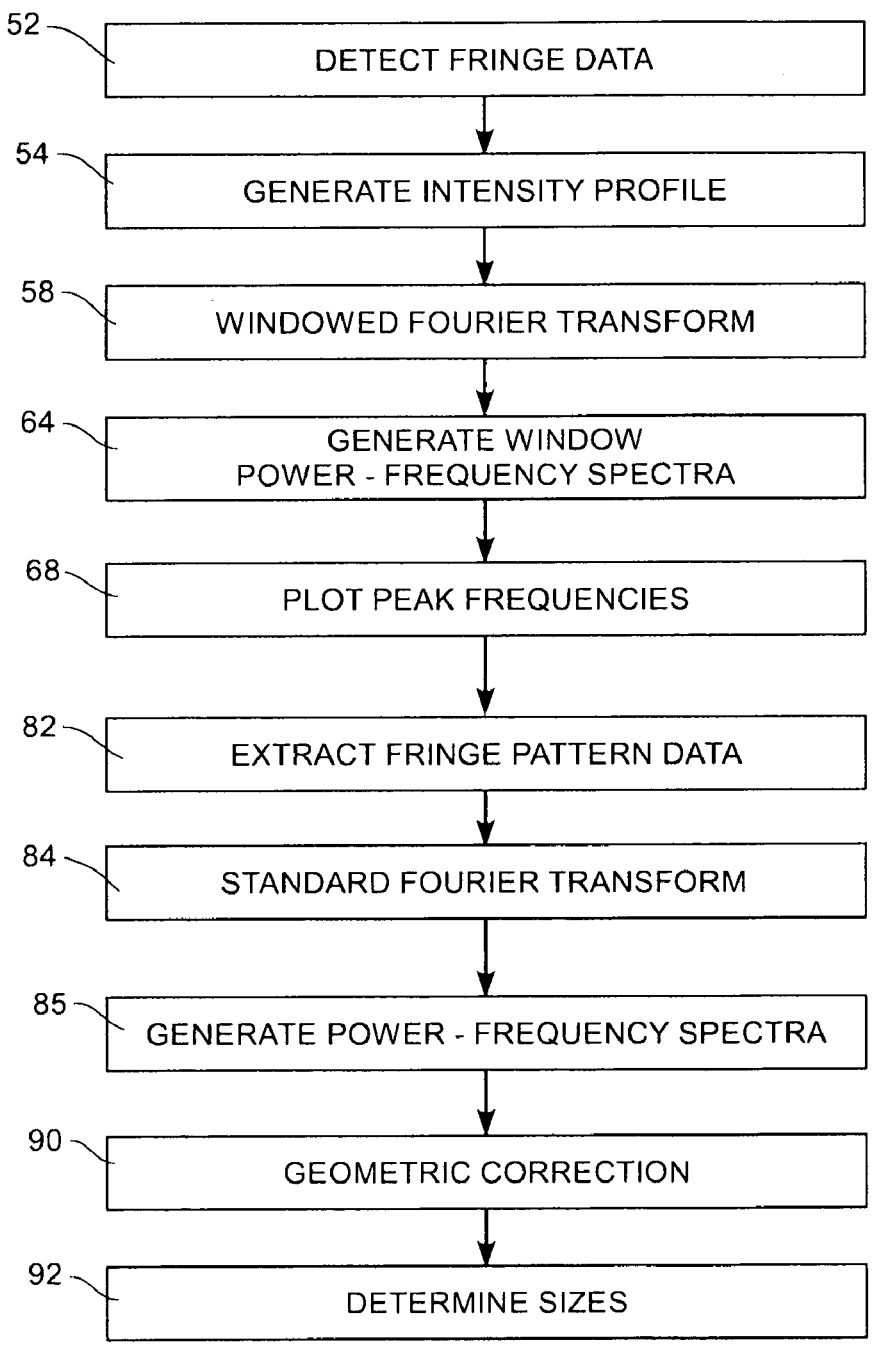
FIG. 1 is a flowchart illustrating a process for analyzing the fringe pattern data in accordance with an embodiment of the present invention.

Turning now to the drawings, FIG. 1 is a flowchart illustrating a preferred process for analyzing fringe pattern data to obtain the desired physical information, for example particle sizes in the interferometric particle sizing application. The original fringe pattern data are largely associated directly with particle size or velocity or other physical information depending on the application, and therefore are useful. However, the fringe pattern data also include extraneous data associated with noise, non-spherical particles, and multi-particle effects. Most extraneous data are of limited or no utility and complicates the analysis of fringe pattern data. According to an embodiment of the present invention, windowed Fourier transforms and peak frequencies are employed to distinguish the useful data from the extraneous data and extract the useful data. Subsequent processing steps are performed only on the extracted data, resulting in more reliable particle and droplet characterizing information.

The first step, as indicated at 52, is the detection of scattered light. In one embodiment, this entails forming a two-dimensional image at the sensing plane of an area detector such as a by a CCD (charge coupled device) detector. In alternative systems, the fringe pattern data may be generated, for example, by a point detector such as a photomultiplier tube (PMT) or an avalanche photo detector (APD), a linear CCD detector, or an area detector other than a CCD detector such as a CMOS (complementary metal oxide semiconductor) imaging device.

Figure 2:
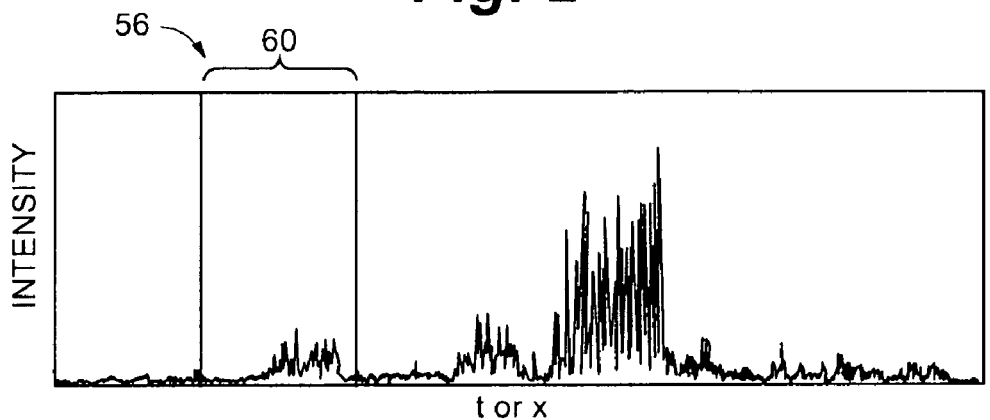
FIG. 2 illustrates a one-dimensional intensity profile (intensity vs. time t or intensity vs. position x) recorded by a point detector over time, a line detector or an area image sensor.

At 54 the recorded fringe pattern information is used to generate a one-dimensional intensity profile 56 as seen in FIG. 2, where an intensity is plotted on the ordinate against an abscissa parameter. The abscissa parameter may be a spatial parameter such as distance or pixel if a line or area detector is used, or the abscissa parameter may be time if a point detector is used. Furthermore, when the fringe information is recorded with a two-dimensional area detector, the intensity profile is obtained by vertically scanning (combining or integrating) a small number of neighboring horizontal rows in the two-dimensional image to produce one-dimensional intensity data. Such vertical scanning may be used to analyze the whole image.

Next at 58, a windowed Fourier transform is performed on the fringe pattern data as represented by the intensity profile. Performing a windowed Fourier transform can be thought of as executing multiple standard Fourier transforms, each upon a window or continuous subset 60 of the intensity profile 56 at a different one of multiple window positions. The window positions are incremented along the abscissa to cover the complete length of the profile. Each window position is characterized by an abscissa parameter midpoint.

Each Fourier transform is performed only upon data within the associated window, and involves multiplying that data by a window function. The present system employs the 64-sample or 64-pixel Hann window, which is non-zero within the window width and zero outside the window. Other window sizes, e.g. 32 samples or 128 samples, and other window functions, e.g. Hamming window or Blackman window, may be used. In any case, the window width is a continuous fraction or subset of the intensity profile length as measured in pixels corresponding either to time or distance.

Figure 3:
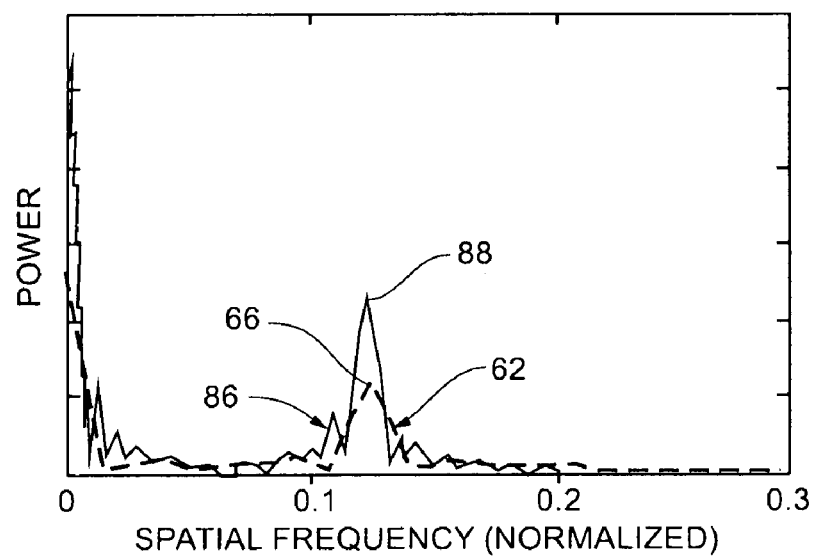
FIG. 3 illustrates a space-frequency distribution for a subset and an abscissa parameter segment of the intensity profile of FIG. 2.

After the windowed Fourier transforms are performed at all window locations, a window power-frequency spectrum 62, denoted by the dashed line in the graph in FIG. 3, is generated at 64 in for each window and correlated with the midpoint of the window location at the abscissa parameter. A dominant or "peak" frequency corresponding to a frequency at which the power of the power-frequency spectrum 62 is at a maximum is found in each of the spectra, as indicated at 66 in FIG. 3.

Figure 4:
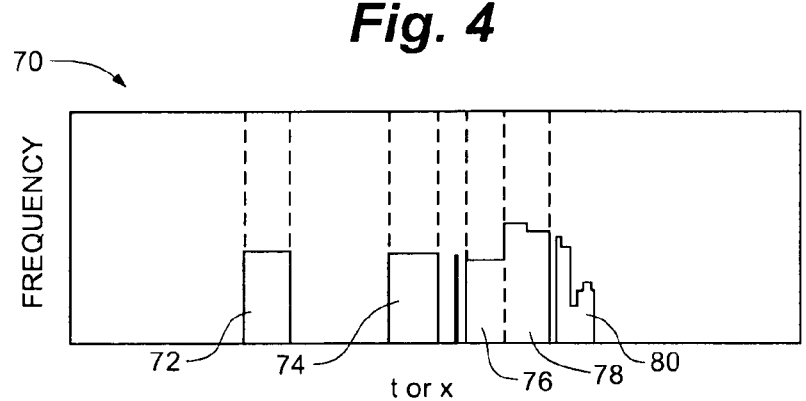
FIG. 4 is a plot of peak frequencies in the abscissa-frequency domain over the full range of the intensity profile of FIG. 2.

Then, as indicated at 68, the peak frequencies are plotted or recorded in an abscissa-frequency domain (i.e. space-frequency or time-frequency domain) to produce a ridge map or abscissa-frequency profile 70 of the peak frequencies as depicted in FIG. 4. If a "peak frequency" is associated with a window location unlikely to be part of a fringe pattern, for example locations of low amplitude (i.e. below a predetermined threshold) or lacking a perceptible intensity oscillation, the frequency is assigned a value of zero in the ridge map or abscissa-frequency profile 70, to more clearly separate useful data from extraneous data.

The peak (dominant) frequency plot in FIG. 4 has identified abscissa parameter segments at 72, 74, 76 and 78. Abscissa parameter segments 76 and 78 correspond to fringe patterns that overlap, but are distinguishable based on their different peak frequencies. With each fringe pattern having a primary frequency that is substantially constant, segments indicating fringe patterns are likely to have constant frequency or zero slope as indicated for abscissa parameter segments 72, 74 and 76. The "two-tiered" top of abscissa parameter segment 78 illustrates a change in the peak frequency within a predetermined tolerance, so that a fringe pattern is recognized. A segment 80 is rejected, i.e. determined not to represent a fringe pattern, due to the variance in peak frequency.

At 82 (FIG. 1), the space or time locations of segments 72-78 are applied to the intensity profile (FIG. 2) to distinguish and extract those segments of the original fringe data determined to represent fringe patterns. Each segment is padded with zeros (i.e. assigning a value of zero to elements outside the fringe pattern) on both sides to fix its length, e.g. at 512 samples. Then, as indicated at 84, the original fringe data within each of segments 72-78 are analyzed in a frequency domain by performing a standard Fourier transform on the data within that segment. At 85, power-frequency spectra associated with segments 72-78 are generated and the peak frequency of each fringe pattern data segment is obtained. The result with respect to one of the data segments is a power-frequency spectrum 86 that indicates the peak frequency at 88, denoted by the solid-line plot in FIG. 3. This frequency information can be used to calculate particle size or velocity or other physical quantity or information based on a known relationship depending on the underlying physics of the application.

As an alternative to performing standard Fourier transform, each extracted segment of the original fringe data can be analyzed in a space domain by autocorrelation.

Because of the improved resolution due to the greater number of sample points in segments 72-78 as compared to the window power-frequency spectrums 62, peak frequency 88 is a more accurate determination of the dominant frequency than is peak frequency 66.

For fringe patterns that are captured in the spatial domain, conversion of the imaged fringe spacing to the angular fringe spacing involves implementing a geometric correction, a step indicated at 90 in FIG. 1. In a processing step 92, the corrected information is used to determine droplet sizes or other information. The methodology for the geometric correction 90 and processing step 92 is described below in connection with FIG. 8 and equations (1) through (6).

Figure 5:
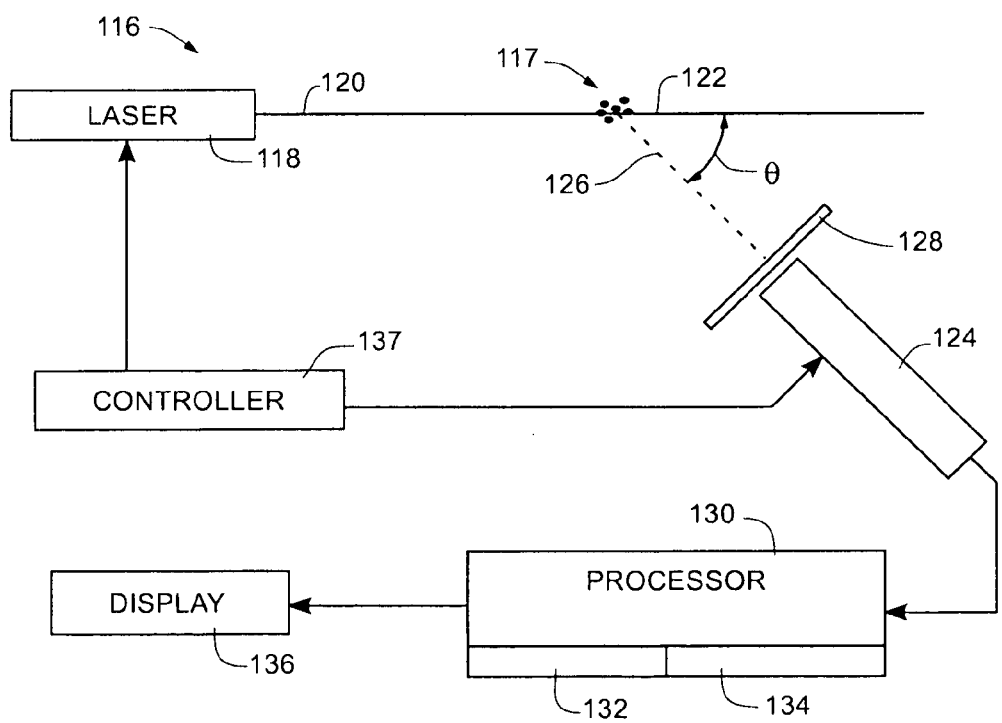
FIG. 5 is a schematic view of an interferometric particle sizing system configured according to the present invention.

Referring to FIG. 5, an embodiment of an interferometric droplet measuring system 116 for measuring droplet sizes is depicted including an irradiation source such as a laser 118, e.g. a 532 nm double-pulsed Nd:YAG laser. Laser 118 incorporates beam shaping optics for generating a laser beam 120. The laser beam appears as a line in the figure, and occupies a plane perpendicular to the drawing to provide a planar light sheet 122 within a viewing volume traversed by liquid (e.g. water) droplets 117 or other particles. The light sheet has a thickness in the micron-millimeter range, e.g. 250 or 500 micrometers. Droplets 117 can be produced by a nozzle or other source (not depicted) that causes droplets 117 to travel at least generally parallel to the plane of light sheet 122. Alternatively, droplets 117 can be carried in a turbulent flow along and through the light sheet. In either event, droplets 117 within the light sheet scatter the laser energy by refraction and reflection.

System 116 may include a digital camera 124 such as a CCD (charge-coupled device) camera (e.g. 12 bit, 2,000×2,000 pixels) and have an optical system 125 that collects and detects scattered energy. A lens axis or optical axis 126 of the camera lies in the plane of FIG. 5 and is inclined from the plane of light sheet 122 by a scattering angle θ of 60 degrees. In accordance with generalized scattering imaging (GSI), 60 degrees is the scattering angle at which the oscillation spacing or frequency of fringe patterns exhibits minimum sensitivity to changes in the refractive index of droplets under study.

An aperture plate 128 is disposed upstream of digital camera 124 and incorporates an elongate, slot-like aperture oriented lengthwise along the plane of FIG. 5. Thus, scattered light reaching camera 124 is restricted to that passing through the elongate aperture.

Figure 6:
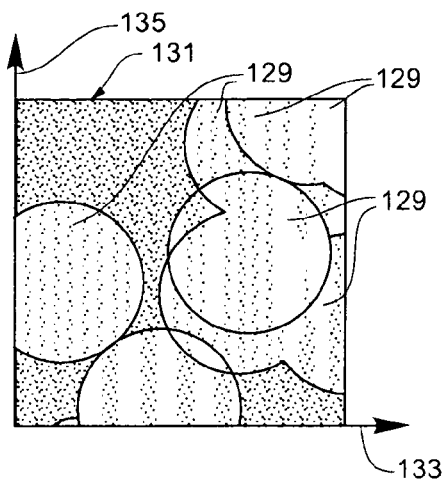
FIG. 6 illustrates out-of-focus interferometric fringe pattern images produced by an interferometric particle sizing instrument with a conventional circular aperture.
Figure 7:
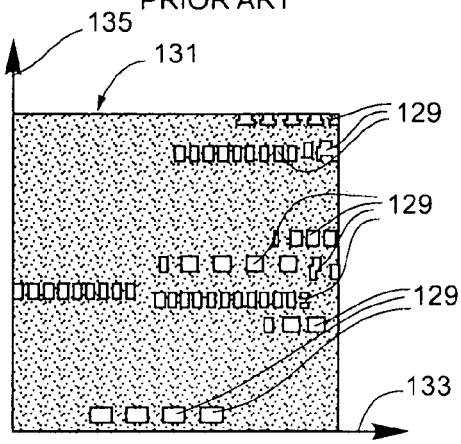
FIG. 7 depicts out-of-focus interferometric fringe pattern images produced by the system of FIG. 5.

The purpose of aperture plate 128 is to crop the disk-shaped fringe pattern images 129 that correspond to droplets 117, to improve the capacity to distinguish between separate fringe pattern images. To illustrate this result, FIGS. 6 and 7 represent fringe pattern images 129 that are out of focus and subtended by a plane 131 having a first or horizontal axis 133 perpendicular to a second or vertical axis 135. The fringe pattern images 129 of FIGS. 6 and 7 were produced using a conventional round aperture and slotted aperture plate 128, respectively. Considering first FIG. 6, light scattered by each droplet produces an out-of-focus fringe pattern image in the shape of a disk. The size of the out-of-focus fringe pattern images 129 subtended by the plane 131 depends on camera optics, and accordingly the fringe pattern images are the same size regardless of variations in the diameters of droplets 117. In contrast, different fringe pattern images have different fringe patterns or oscillation patterns, as represented by the alternating light and dark vertical stripes of the fringe pattern images 129. Each pattern exhibits a substantially uniform spacing (more precisely, angular spacing) between fringes or oscillations. The spacing is inversely proportional to the diameter of the droplet 117 producing fringe pattern image 129. The fringe pattern image at the bottom of FIG. 6 corresponds to a droplet smaller than the fringe pattern images immediately above it with more fringes, i.e. closer fringe pattern spacing.

The fringe pattern images 129 in FIG. 7 are equivalent to that in FIG. 6, except that due to aperture plate 128, the formerly circular fringe pattern images are reduced to horizontal bars comprising horizontal center regions of equivalent circular fringe pattern images 129. The fringe pattern spacing appears as clearly as it does in FIG. 6, with the added advantage that the circular patterns overlapping one another in FIG. 6 are reduced to spaced apart horizontal bars in FIG. 7, and thus are more readily distinguished from one another. As an alternative to plate 128, a cylindrical lens can be used to compress each fringe pattern image 129, thereby reducing the incidence of overlapping fringe pattern images.

Returning to FIG. 5, the output of digital camera 124, a digital signal representing the fringe pattern images such as those in FIG. 7, is provided to a processor 130 for at least temporary storage in a memory 132 and processed based on operating programs 134 also stored in the processor. Droplet information generated as a result of the operations on the incoming signal is provided to a video terminal or other display device 136 that provides the information in human readable form. A controller 137 synchronizes laser 118 and digital camera 124.

Figure 8:
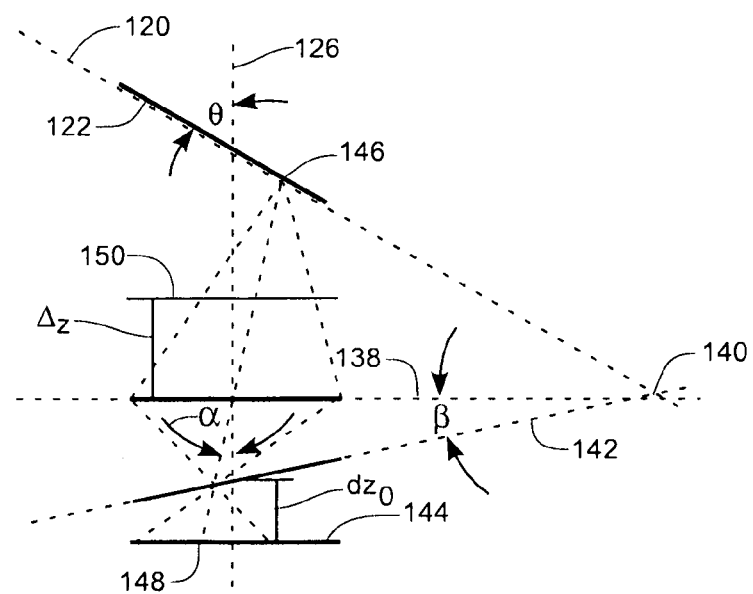
FIG. 8 is an enlarged schematic view depicting the optical system subcomponent of FIG. 5.

FIG. 8 schematically illustrates certain adjustments made to digital camera 124 in the course of using system 116. Because of the 60-degree (rather than 90-degree) scattering angle θ, the light sheet plane 122 and a lens plane 138 of camera 124 are not parallel, but intersect along a line 140 which appears as a point in FIG. 8. Based on the Scheimpflug principle, a focused image plane 142, i.e. the plane where images from light sheet 122 are in focus, also intersects line 140 and is inclined from lens plane 138 by a Scheimpflug angle β. Light scattered by the droplets 117 is imaged on a light sensing plane 144 perpendicular to lens plane 138 and spaced apart from focused image plane 142, thus to produce the desired out-of-focus images.

Along lens axis 126, focused image plane 142 and sensing plane 144 are separated by a nominal defocusing distance dzo. Because of the incline of lens plane 138 relative to light sheet 122, and the resulting incline of sensing plane 144 relative to focused image plane 142, the actual defocusing distance dzx varies with lateral position, increasing in the rightward lateral direction as viewed in FIG. 8. A magnification ratio $M_x$ likewise varies, having a nominal value $M_0$ at the lens axis.

In FIG. 8, a droplet 146 spaced apart from lens axis 126 produces an out-of-focus image 148 on sensing plane 144 that also is spaced apart from the lens axis. More particularly, image 144 can be thought of as angularly spaced apart from lens axis 126 by an angle α. The offset from the lens axis distorts image 144, and the distortion may be corrected or taken into account for the image for a more accurate representation of the fringe pattern spacing. An in-situ calibration to provide direct conversion from a fringe pattern spacing across a fringe pattern image to the corresponding angular fringe pattern spacing Δλ is desirable, but difficult to implement. One aspect of the present invention is a geometric optics-based correction process that compensates for the image distortion.

As a first step in the geometric correction process, the system is calibrated using a calibration target to determine a pre-defocusing magnification ratio M corresponding to lens plane 138 positioned at an initial calibration plane 50, spaced apart axially from light sheet 22 by a distance $d_o$ determined by the equation $$d_o = (1+1/M)f, \quad (1)$$

where f is the lens focal length. Then, based on the magnification ratio M and a defocusing shift Δz (i.e. the axial distance between calibration plane 150 and lens plane 138), the nominal defocusing plane $dz_0$ and post-defocusing nominal magnification Mo are determined. Then, the defocusing distance and magnification at any given angle α offset from the lens axis are calculated according to the following equations:

$$dz_x = dz_o + (1+M_o) \cdot f \cdot \sin\alpha[\sin\alpha - \cos\alpha \cdot \tan(\alpha+\beta)]; \text{ and} \quad (2)$$

$$M_x = M_o - (1+M_o) \cdot \sin\alpha \cdot [\sin\alpha - \cos\alpha \cdot \tan(\alpha+\beta)] \quad (3)$$

Thus, for any point along sensing plane 144 spaced laterally from lens axis 126, i.e. offset from the lens axis by a given angle α, the defocusing distance and magnification are corrected from $dz_0$ to $dz_x$ and from $M_0$ to $M_x$ to compensate for the relative incline of the sensing plane to the focused image plane.

At this stage, the angular spacing of the fringes of the fringe pattern is calculated, based on the corrected values for defocusing distance and magnification, using the equation:

$$\Delta\upsilon = M_x \cdot n \cdot \delta / dz_x \quad (4)$$

where Δυ is the angular fringe pattern spacing in radians; $M_x$ is the magnification at the given point; n is the detected fringe pattern spacing of the image expressed as a number of pixels; and δ is the pixel size in terms of distance (e.g. millimeters) between adjacent pixels.

Conversion of the fringe pattern frequency (spacing) obtained in 185 (FIG. 1) to the angular fringe spacing involves implementing the above-described geometric correction (Equations 1 to 4). At this stage, droplet diameters can be calculated based on the equation:

$$D = \lambda \cdot X / \Delta\upsilon \quad (5)$$

where D is the droplet diameter; λ is the wavelength of the laser energy; Δυ is the angular fringe pattern spacing; and X is a dimensionless factor that depends on the refractive index and scattering angle θ. Given the system scattering angle θ of 60 degrees at which sensitivity to the refractive index is minimized, a constant value of 1.129 can be substituted for X, resulting in the equation:

$$D = 1.129 \cdot \lambda / \Delta\upsilon \quad (6)$$

In general, system 116 can measure droplet diameters over a range of diameters from 10 microns to 600 micrometers. Due to the cropping or otherwise vertical narrowing of fringe pattern images and the separation of spatially proximate fringe patterns having different frequencies, system 116 can be used to characterize sprays having densities much higher than those susceptible to analysis by conventional systems. Field results suggest that system 116 is capable of measuring droplets at concentrations up to about 3,000 droplets per cubic centimeter.

Figure 9:
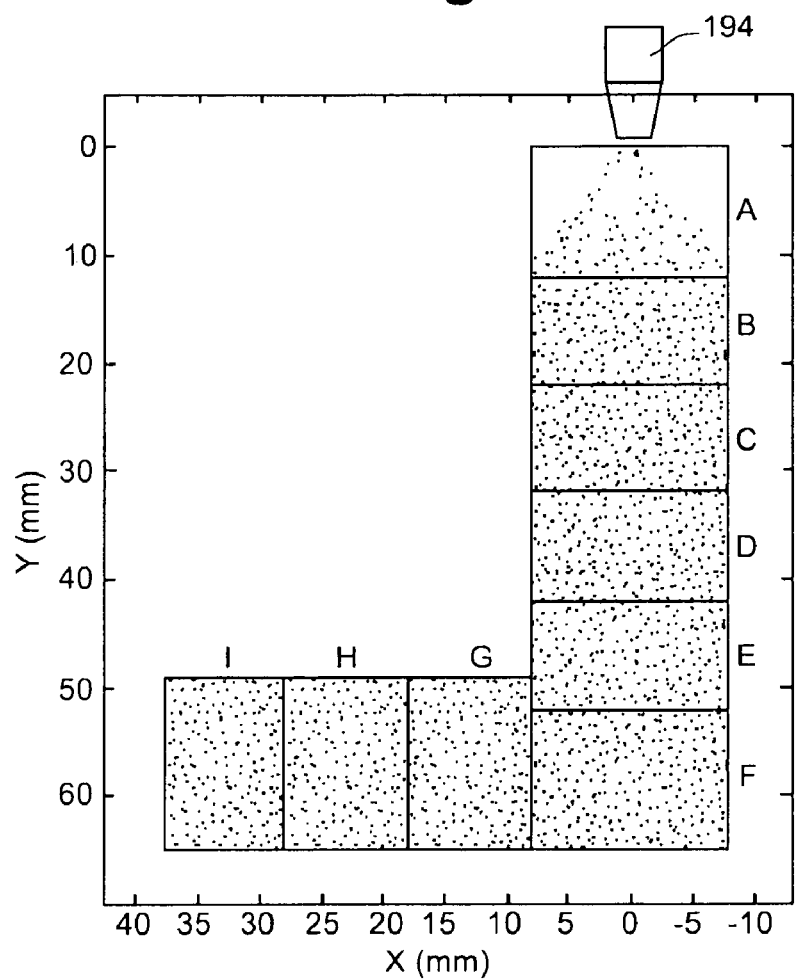
FIG. 9 is a chart illustrating droplet imaging locations with respect to a nozzle of a pressure atomizer.

FIG. 9 illustrates multiple water droplets imaged at a series of image areas A-I with respect to a nozzle 194 of a pressure atomizer. Each point in one of areas A-I corresponds to a droplet detected and measured by system 116.

Figure 10:
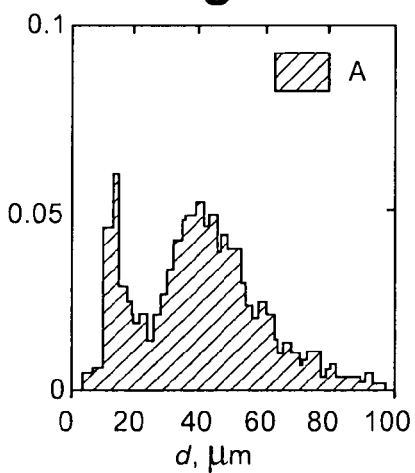
FIGS. 10-12 are histograms corresponding to different zones of the image of FIG. 9.
Figure 11:
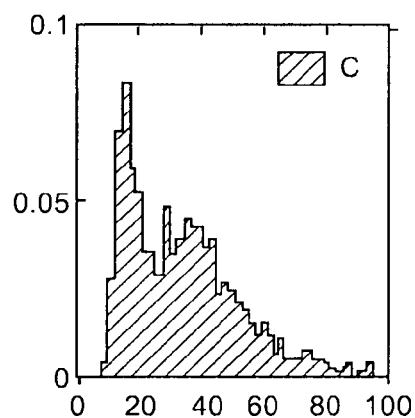
Figure 12:
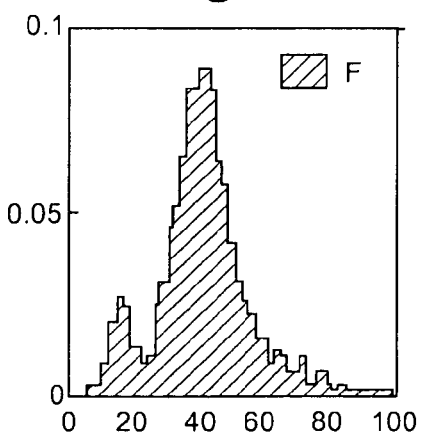

Measured diameter histograms corresponding to regions A, C, and F (FIGS. 10, 11 and 12) indicate dual peaks corresponding to larger droplets (D=45 microns) in a spray sheet area near the nozzle exit, and smaller droplets (D=15 microns) in a recirculation zone surrounded by the spray sheet. Region C lies downstream, disposed primarily in the recirculation zone, and the peak corresponding to the smaller diameter droplets is higher. Further downstream in region F, a hollow conical region of the spray closes, and the peak associated with the larger droplets becomes dominant.

Figure 13:
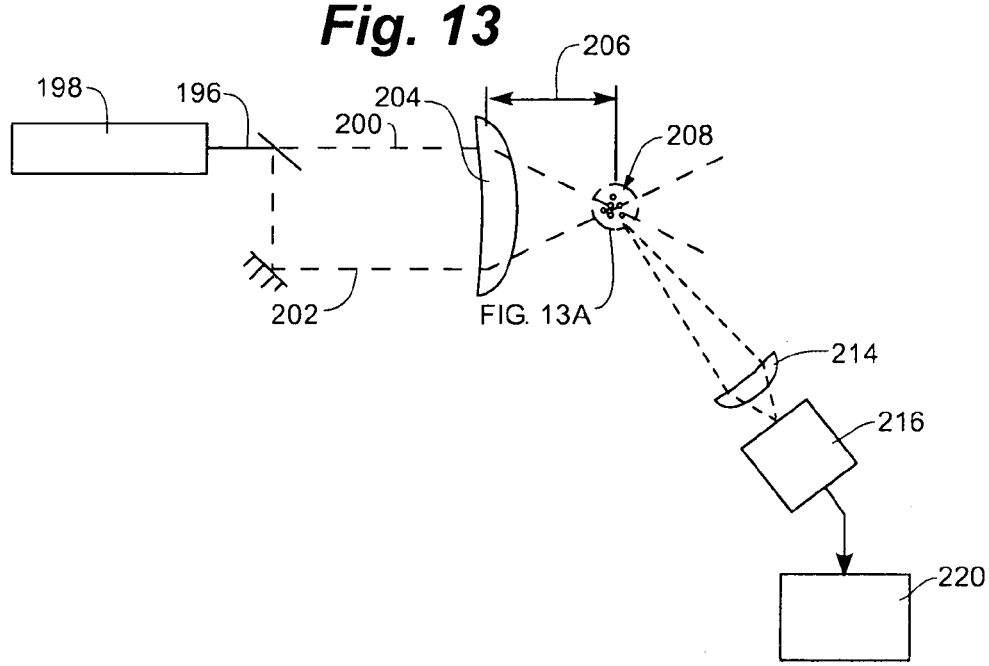
FIG. 13 depicts a laser Doppler velocimeter according to the present invention.
Figure 13A:
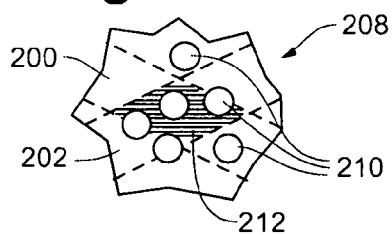
FIG. 13a depicts the measuring region of the laser Doppler velocimeter of FIG. 13.

The invention may also be embodied in a laser Doppler velocimetry system, such as depicted in FIG. 13. Laser Doppler velocimetry (LDV) is an established technique for particle and fluid flow velocity measurements. To measure one component of velocity, a single beam 196 from a laser 198 is split into two parallel beams 200 and 202 and passed through a transmitting lens 204 having a focal length 206, causing the parallel beams 200 and 202 to cross at an intersection 208. The intersection 208 defines the measuring region of the system. A particle or particles 210 passing through the intersection 208 scatters light in all directions. Each particle passing through the measuring region moves through a fringe pattern 212 generated by the interference of the two split beams 200 and 202. A portion of the scattered light is collected by a receiving lens 214 and directed to irradiate a photo detector 216.

Figure 14:
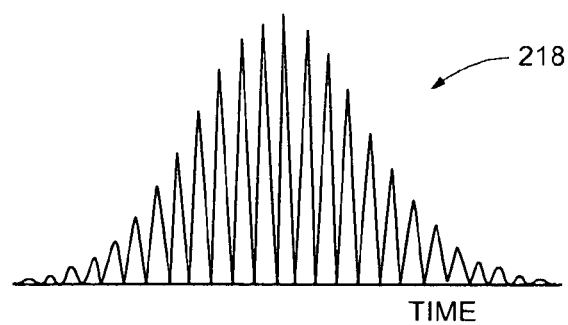
FIG. 14 illustrates the oscillation pattern generated by the scattered light from particles passing through the measurement volume in the laser Doppler velocimetry system of FIG. 13.

In response to the irradiation by the scattered light, the photo detector 216 outputs an oscillation signal 218, depicted in FIG. 14. The oscillation signal 218 is proportional to the intensity of the collected light scattered from the fringe pattern 212. The oscillation signal 218, also known as a Doppler burst signal, serves as the signal source for a velocity measurement. A signal processor 220 can use the algorithm of FIG. 1 to detect the oscillation signal and then process it to obtain the oscillation frequency. Because the oscillation frequency is the inverse of the time required to cross a pair of fringes, the velocity component v normal to the fringes is given by:

$$v = d_f f_D \quad (7)$$

where $d_f$ is the known spacing of interference fringes, $f_D$ is the oscillation frequency.

Hence, the method depicted in FIG. 1, which entails the identification of oscillation patterns and the determination of oscillation frequencies, is applicable in LDV systems. Moreover, the ability of the present invention to discern overlapping fringe patterns enables the LDV technique to be employed in a dense particle field.

While the foregoing embodiment has been described in terms of interferometric measurement of droplet size and laser Doppler measurement of particle velocity, it is to be recognized that the principles of the invention apply to a wide variety of particle and droplet measuring techniques that employ the analysis of signals of oscillation pattern produced by, or derived from, scattered coherent light.

What is claimed is:

1. A method for analyzing a fringe or oscillation pattern comprising: performing a plurality of windowed Fourier transform analyses on a plurality of unique subsets of a one-dimensional intensity profile, each of said plurality of windowed Fourier transform analyses being performed on one of said plurality of unique subsets; generating an abscissa-frequency profile; identifying an abscissa parameter segment of said abscissa-frequency profile having a substantially constant frequency greater than zero; performing a standard Fourier transform analysis on said one-dimensional profile across said abscissa parameter segment; identifying a peak frequency from said standard Fourier transform analysis; and deriving a physical quantity from said peak frequency.

2. The method of claim 1, wherein generating an abscissa-frequency profile comprises:
   identifying a set of dominant frequencies, one within each of said unique subsets; and
   generating said abscissa-frequency profile from said set of dominant frequencies.

3. The method of claim 1 wherein said subsets overlap each other in the domain of said abscissa parameter of said abscissa-frequency profile.

4. The method of claim 1 wherein each of said subsets comprises a continuous portion of said one-dimensional intensity profile.

5. The method of claim 1 wherein said abscissa parameter is a time parameter.

6. The method of claim 5 wherein said physical quantity is a velocity.

7. The method of claim 1 wherein said abscissa parameter is a spatial parameter.

8. The method of claim 7 wherein said physical quantity is a particle size or a droplet size.

9. The method of claim 8 wherein a fringe spacing is determined from said peak frequency and said droplet size or particle size is derived from said fringe spacing.

10. The method of claim 7 further comprising:
    providing an electromagnetic radiation measuring device that measures a plurality of radiation intensities with a matrix of sensors on a sensing plane, said sensing plane being defined by a first axis and a second axis; and
    scanning said array of sensors in a direction defined by said second axis to obtain said one-dimensional intensity profile.

11. A method of analyzing overlapping fringe or oscillation patterns, comprising:
    (a) performing a windowed Fourier transform analysis on a subset of a one-dimensional intensity profile to determine a power-frequency spectrum of said subset;
    (b) identifying a dominant frequency within said power-frequency spectrum of said subset;
    (c) repeating steps (a) and (b) for a plurality of unique subsets across said one-dimensional intensity profile to obtain an abscissa-frequency profile;
    (d) identifying a plurality of abscissa parameter segments of said abscissa-frequency profile having substantially constant dominant frequencies greater than zero;
    (e) identifying a plurality of peak frequencies, one for each of said abscissa parameter segments; and
    (f) determining a physical quantity from each of said peak frequencies.

12. The method of claim 11 wherein said dominant frequency is selected from a predetermined range of frequencies.

13. The method of claim 11 wherein the abscissa parameter of said abscissa parameter segment is a time parameter.

14. The method of claim 13 wherein said physical quantity is a velocity.

15. The method of claim 11 wherein the abscissa parameter of said abscissa parameter segment is a spatial parameter.

16. The method of claim 15 wherein said physical quantity is a particle size or a droplet size.

* * * * *